(12) United States Patent
Lang et al.

(10) Patent No.: US 7,512,449 B2
(45) Date of Patent: Mar. 31, 2009

(54) MEDICAL ELECTRODE

(75) Inventors: Burrhus Lang, Innebruck (AT);
Markus Wilfinger, Innsbruck (AT)

(73) Assignee: Leonhard Lang KG, Archenweg (AT)

( * ) Notice: Subject to any disclaimer, the term of this patent is extended or adjusted under 35 U.S.C. 154(b) by 213 days.

(21) Appl. No.: 11/152,690

(22) Filed: Jun. 13, 2005

(65) Prior Publication Data
US 2006/0030767 A1    Feb. 9, 2006

Related U.S. Application Data

(63) Continuation of application No. PCT/AT03/00366, filed on Dec. 10, 2003.

(30) Foreign Application Priority Data
Dec. 13, 2002    (AT) .............................. A 1867/2002

(51) Int. Cl.
*A61N 1/04*    (2006.01)
(52) U.S. Cl. ....................... 607/152; 607/115; 600/382; 600/391
(58) Field of Classification Search ................ 607/115, 607/129, 142, 152
See application file for complete search history.

(56) References Cited

U.S. PATENT DOCUMENTS

| 4,122,843 | A |   | 10/1978 | Zdrojkowski |         |
|-----------|---|---|---------|-------------|---------|
| 4,155,354 | A |   | 5/1979  | Rassmussen  | 128/640 |
| 4,442,315 | A |   | 4/1984  | Segawa      | 174/36  |
| 4,934,383 | A | * | 6/1990  | Glumac      | 607/152 |
| 4,944,088 | A | * | 7/1990  | Doan et al. | 29/858  |
| 5,402,780 | A | * | 4/1995  | Faasse, Jr. | 600/392 |
| 5,782,241 | A |   | 7/1998  | Felblinger et al. | |
| 6,453,205 | B1| * | 9/2002  | Dupelle et al. | 607/152 |

FOREIGN PATENT DOCUMENTS

| DE | 197 30 811 C1 | 5/1999 |
| WO | 96/32085      | 10/1996 |

* cited by examiner

*Primary Examiner*—Carl H Layno
*Assistant Examiner*—Brian T Gedeon
(74) *Attorney, Agent, or Firm*—Wenderoth, Lind & Ponack L.L.P.

(57) ABSTRACT

A medical electrode for conducting signals, in particular for conducting signals from the human skin, is built up in at least two layers. A preferably metallic signal conductor can be connected to the signal-emitting subject, preferably in the form of a signal-conducting layer, and is arranged between an upper top layer and an adhesive layer which can be brought into contact with the signal-emitting subject. The electrode has a tapping pad, and an electrically insulating covering element arranged between the tapping pad and the signal-emitting subject, and at least one side of the preferably planar covering element is electrically conductive in construction.

38 Claims, 4 Drawing Sheets

MEDICAL ELECTRODE

CROSS-REFERENCE TO RELATED APPLICATIONS

This application is a continuation of International Application No. PCT/AT2003/000366, filed Dec. 10, 2003, which claims priority to Austrian Application No. A 1867/2002, filed Dec. 13, 2002, both of which are incorporated herein by reference in their entirety.

BACKGROUND OF THE INVENTION

The invention relates to a medical electrode for conducting signals (in particular, for conducting signals from the human skin), which is built up in at least two layers. A preferably metallic signal conductor which can be connected to the signal-emitting subject is arranged between an upper top layer and an adhesive layer which can be brought into contact with the signal-emitting subject. The electrode has a tapping pad, and a preferably electrically insulating covering element is arranged between the tapping pad and the signal-emitting subject.

Known electrodes which can be stuck on to the skin comprise an adhesive layer having an opening for accommodating an electrically conductive gel for contacting the signal-emitting subject, an upper top layer and a signal-conducting layer arranged in between, and have a tapping pad which is formed by the upper top layer and the signal-conducting layer. To prevent the signal-conducting layer, which is freely accessible from the under-side of the tapping pad, from coming into contact with the signal-emitting subject, as a result of which the signal conducted would be influenced, it is conventional to arrange on the side of the preferably electrically non-conducting adhesive layer facing the signal-emitting subject a skin-friendly plaster element which masks the tapping pad and thus prevent contact between the signal-conducting layer and the signal-emitting subject in the region of the tapping pad.

It is furthermore known from DE 197 30 811 C1 to provide the tapping pad with a non-adhesive covering on the side facing the signal-emitting object and to shield the signal-conducting layer of the electrode against external interferences in this manner.

It has been found, however, that the coverings, which as a rule are produced from plastic, for example from PVC, PE or PET, undergo static charging during the measuring operation, in particular if the signal-emitting subject moves, as is the case, for example, when carrying out an exercise ECG. This static charging of the covering element has an effect on the signal-conducting layer, with which the covering element is indeed in direct contact, and influences the conducted signal in this manner.

A further disadvantage of the known medical electrodes which have emerged is that the plastics which are used for producing the covering have static properties of varying favorability. Considered from this point of view, PVC is the most suitable for producing the covering. On the other hand, PE or PET are preferred for producing the upper top layer of the medical electrode, inter alia for ecological reasons. In the context of a simple and inexpensive production process, it would be appropriate to construct the upper top layer and the covering in one piece, which in practice leads to either an electrode having a high-quality upper top layer but poorer static properties for the covering, or an electrode having a high-quality covering but a less suitable upper top layer.

SUMMARY OF THE INVENTION

On the basis of this prior art, the object of the invention is to provide a novel medical electrode which allows shielding of the signal-conducting layer against external interference signals, while avoiding the disadvantages described above, and at the same time is inexpensive to produce.

This object is achieved according to the invention in that at least one side of the preferably planar covering element is electrically conductive in construction, which prevents the covering from becoming statically charged and the conducted signal from being influenced or modified. In this context it is primarily not a matter of how the electrically conductive side of the covering element is constructed, but rather the fact that the covering element has a conductive side is essential to the invention. Thus, the electrically conductive side of the covering element can be formed, for example, by an electrically conductive element having a grid-like construction, or by an electrically conductive foam. However, the use of a thin metal strip or a textile sheet-like structure with metal threads running through it would also be just as conceivable, like the use of a conductive covering element which is conductive throughout—for example a carbon conductor—or the printing of an electrically conductive layer on to the covering element. In contrast to the prior art, due to the electrically conductive construction of one side of the covering element, what static properties the plastic used for producing the covering element has is no longer relevant, so that plastics which are less suitable from the static point of view can also be employed in the production of a covering element constructed in one piece with the top layer.

According to a preferred embodiment of the invention, the covering element is constructed as a preferably two-layered film having a first electrically insulating carrier layer and a second electrically conductive layer, it being possible for the electrically insulating layer to be adhesive in construction, so that the covering film can be stuck on to the side of the tapping pad facing the signal-emitting subject in a simple manner regardless of the rest of the production process. At the same time, such a construction of the covering element allows conventional medical electrodes already in circulation to be equipped with a covering element which has an electrically conductive side.

So that the electrically conductive side of the covering element does not influence the signal conductor and therefore the signal conducted, according to a preferred embodiment of the invention, the electrically conductive side of the covering element is separated galvanically from the signal conductor. The electrically insulating carrier layer of a covering element constructed as a film of at least two layers or the covering element itself is suitable in particular for this galvanic separation, so that in a cross-sectional view of the tapping pad the signal conductor and the electrically conductive side of the covering element are arranged with vertical spacing from one another, preferably overlapping at least in regions.

As is known per se, according to one embodiment of the invention, the signal conductor can be connected to the signal-emitting subject via an electrically conductive gel which can preferably be arranged in an opening of the adhesive layer, and the tapping pad can have a tapping element, preferably a stud, which is in electrical contact with the signal conductor and is accessible from the side of the electrode facing away from the signal-emitting subject.

According to a further embodiment of the invention, the covering element is connected, preferably glued on, to the tapping pad. This results in a particularly reliable shielding of the signal conductor, especially if the electrically conductive side of the covering element extends at least in part to the upper side of the upper top layer.

If the covering element or the carrier layer of the covering element is constructed in one piece with the upper top layer of the electrode, this has a favourable effect on the production costs (as already mentioned).

In order to avoid as far as possible reddening of the skin of the patient, which may be caused by the adhesive layer, in a further embodiment of the invention, a skin-friendly, electrically insulating plaster element is arranged on the side of the adhesive layer facing the signal-emitting subject. In this case, a simple structure of the electrode according to the invention results if the covering element or the electrically insulating carrier layer of the covering element is formed by the plaster element. The side of the part of the plaster element masking the covering pad which faces the tapping pad is thus electrically conductive in construction. In this case the electrical side in turn can be constructed as a grid-like electrically conductive element, as a metallic strip, as an electrically conductive foam or the like. A covering element constructed as a two-layered film can likewise be glued in a simple manner on to the part of the plaster element masking the tapping pad. To prevent the signal conductor from coming into contact with the electrically conductive side of the covering element arranged on the plaster element in this embodiment of the invention, the side of the tapping pad facing the signal-emitting subject can be provided, as is known per se, with a covering of plastic.

In a further embodiment of the invention, in the case of medical electrodes for conducting signals, in particular for conducting signals from the human skin, having a top layer, an adhesive layer for sticking the electrode on to the skin and a preferably metallic signal conductor which can be connected to the signal-emitting subject, at least the side of the top layer facing away from the signal-emitting subject is electrically conductive in construction at least in regions. A particularly reliable shielding of the signal conductor against interference signals then results if the under-side of the top layer is also electrically conductive in construction at least in regions. As is already the case in the embodiment examples described above, the electrically conductive side(s) of the top layer can be formed by an electrically conductive element having a grid-like construction, an electrically conductive foam, a metallic strip, a textile sheet-like structure with integrated metallic threads, or a printed-on electrically conductive layer.

Construction of the top layer or the electrically conductive side as a preferably two-layered film having a first electrically insulating carrier layer and a second electrically conductive layer is also conceivable. Regardless of how the electrically conductive side(s) of the top layer is (are) constructed, in a further embodiment of the invention, the electrically conductive side of the top layer is separated galvanically from the signal conductor, and electrically conductive separate regions of the top layer which may be present are preferably connected electrically to one another, in order to prevent influencing of the signal conductor by the electrically conductive side of the top layer.

In a further embodiment of the invention, in which the electrode has a tapping pad, a preferably electrically insulating covering element being arranged, preferably glued, on the side of the tapping pad facing the signal-emitting subject, the covering element is constructed in one piece with the top layer. As a result, the covering element produced in one piece with the top layer and therefore also the top layer can be produced from statically unfavorable plastics, such as, for example, PE or PET, since static charging of the covering is almost completely prevented by the electrically conductive side of the top layer.

In order to be able to reliably prevent such a static charging, in a particularly preferred embodiment of the invention, at least one side of the preferably planar covering element is electrically conductive in construction, the electrically conductive side of the covering element being separated galvanically from the signal conductor.

If the electrically conductive side of the top layer, the signal conductor, and the electrically conductive side of the covering element are arranged with vertical spacing from one another, preferably overlapping at least in regions, this arrangement results in an effect which substantially corresponds to the effect of a Faraday shield, since the sides of the top layer and of the covering element facing away from the signal conductor are electrically conductive in construction, and the sides of the top layer and of the covering element facing the signal conductor are kept nearly free from interference signals in this manner.

According to a further embodiment, a signal conductor which is almost completely shielded from external interferences can also be achieved if a skin-friendly electrically insulating plaster element which at least partly masks the tapping pad is arranged on the side of the adhesive layer facing the signal-emitting subject, the part of the plaster element which masks the tapping pad being electrically conductive in construction on its side facing the tapping pad. This embodiment will be used above all in the subsequent application of a covering film having an electrically conductive side to medical electrodes which are already on the market, and indeed both on the top side as well as on the part of the plaster element masking the tapping pad.

In a further embodiment of the invention, a medical electrode for conducting signals, in particular for conducting signals from the human skin, having a top layer, an adhesive layer for sticking the electrode on to the skin and a preferably metallic signal conductor which can be connected to the signal-emitting subject, and preferably having a tapping pad is equipped with at least one additional electrically conductive layer which is preferably arranged in the form of a Faraday shield or cup and which shields the signal conductor against interference signals.

To conduct the interference signals from or to ground the electrically conductive layer, which is preferably separated galvanically from the signal conductor, in a further embodiment of the invention, the electrically conductive layer is constructed such that it can be brought into contact with a conductor for conducting the electrical interference voltage or interfering electrical activity or interfering electrical potentials. For this purpose, the electrically conductive layer advantageously has a connection element for detachable fixing of the conductor.

A particularly easy handling results if the signals of the signal conductor and the interference signals of the electrically conductive layer are transmitted via a lead which has two galvanically separated conductors. As a result of this arrangement, only one cable from each electrode leads to the evaluation unit, which is of great advantage particularly in the case of measurements during sports activities.

In this case, the lead is advantageously formed by a coaxial cable in which the two galvanically separated conductors of the lead are arranged or constructed coaxially, it being possible for the inner conductor to be brought into contact with the signal conductor, while the outer conductor of the cable is in contact with the electrically conductive layer. With this arrangement, it is possible to prevent movements in or of the contact region of the lead from being able to lead to interferences in the measurement signal, since electrical interference voltages, electrical activities, or electrical potentials which occur are conducted via the electrically conductive layer and the outer conductor of the lead. This means that the movements of the lead or of the contact elements of the lead relative to the electrode, which influenced the conducted signal according to the prior art to date, now have almost no effect on the conducted signal in an electrode according to the invention, or can be ignored completely.

The lead can be brought into contact with the electrode quickly and easily if the lead has a connection element by means of which the electrically conductive layer and the signal conductor can be brought into contact simultaneously with their corresponding conductors of the lead, as in a further embodiment.

BRIEF DESCRIPTION OF THE DRAWINGS

Further advantages and details are explained in more detail with the aid of the following description with reference to the figures shown in the drawings, in which.

DETAILED DESCRIPTION OF THE INVENTION

Figure 1A:
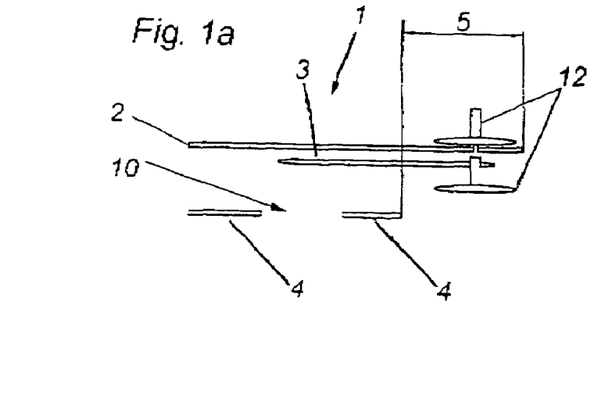
FIG. 1a to 1c show a medical electrode according to the prior art without a covering element for the tapping pad.
Figure 1B:
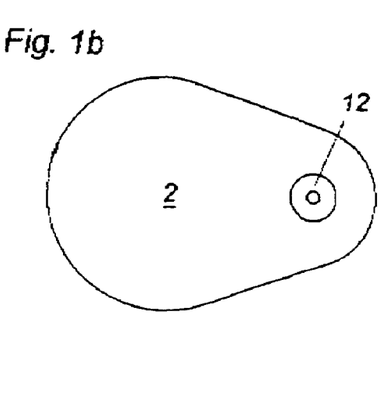
Figure 1C:
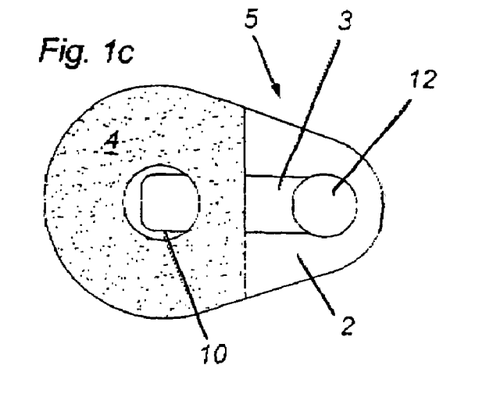

The medical electrode 1 according to the prior art shown in FIG. 1a to 1c is built up in three layers and has a top layer 2 facing away from the skin of the patient and an adhesive layer 4, with which the electrode 1 is fixed on to the skin of the patient. A signal conductor 3 is arranged between these two layers 2, 4. The signal conductor 3 is in contact with the skin of the patient, for example via a conducting gel (not shown), which is arranged in an opening 10 of the adhesive layer 4. The electrode 1 has a tapping pad 5, which is formed by a section of the top layer 2 and a section of the signal conductor 3, and a tapping element 12, for example in the form of a two-part pushbutton riveted together, the upper part of which can be constructed as a stud. Construction of the tapping pad 5 for connection of an electrical wire with a crocodile clip would also be possible as an alternative.

Arrangement of a plaster element (not shown) on the side of the adhesive layer 4 facing the skin of the patient is also possible. In this case, it is favorable to construct the plaster element such that it masks the tapping pad 5 and prevents contact of the signal conductor 3 with the skin of the patient in this manner.

FIG. 1b shows the plan view of the electrode 1, in which only the top layer 2 and the upper part of the pushbutton 12 are visible. If the electrode is viewed from the under-side, as shown in FIG. 1c, it is seen that the top layer 2, apart from in the region of the tapping pad 5, is covered by the adhesive layer 4 up to the opening 10. The opening 10 serves for arrangement of the conductive gel (not shown) which establishes the contact between the skin of the patient and the signal conductor 3 through the adhesive layer 4. In the region of the tapping pad 5, the signal conductor 3, via which the lower part of the riveted pushbutton 12 is connected to the skin of the patient, is arranged on the under-side of the upper top layer 2. In the case of an electrode 1 of such construction, the signal conductor 3 is exposed to external interference signals in an unprotected manner.

Figure 2A:
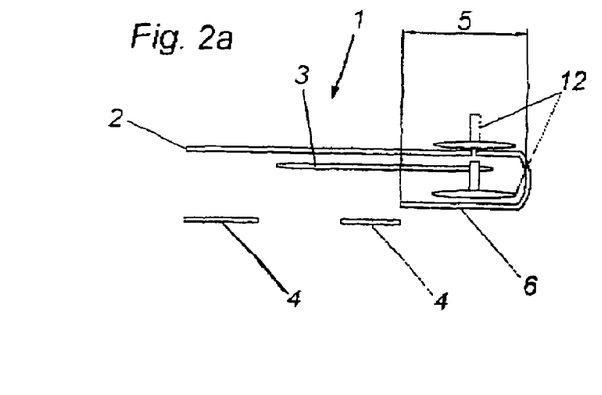
FIG. 2a to 2c show a medical electrode according to the prior art with a covering element for the tapping pad.
Figure 2B:
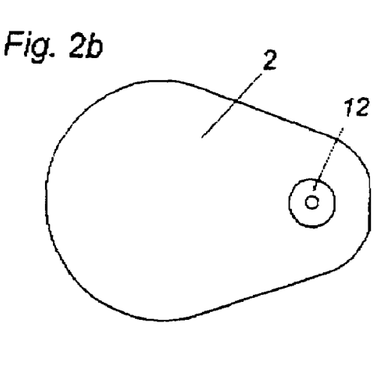
Figure 2C:
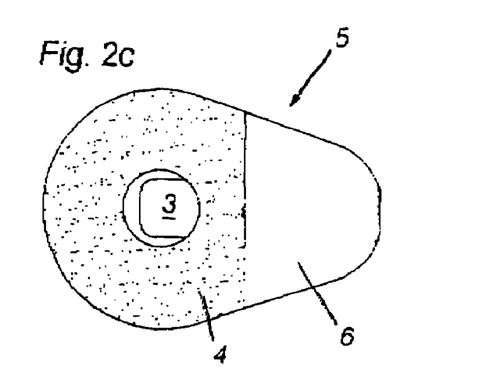

A medical electrode 1 in which the signal conductor 3 is protected against external interferences by means of a covering 6 can be seen from FIG. 2a to 2c. In this case, the covering 6 is produced in one piece with the top layer 2 and is formed by this. As already mentioned, in electrode 1 of such construction the covering 6 or the top layer 2 becomes statically charged and, since it is indeed in contact with the signal conductor 3, influences the signal conducted from the skin of the patient via the signal conductor 3 and the tapping element 12 of the tapping pad 5, so that the measurement results achieved are not reliable. In contrast to the medical electrode shown in FIG. 1c, it can be seen from FIG. 2c, which shows the under-view of the medical electrode 1 shown in FIG. 2a, that the tapping pad 5 is provided with a covering 6 on its side facing the skin of the patient. This covering 6 can be constructed in one piece with the upper top layer 2, as shown, but the arrangement of a separate covering 6 is also possible.

Figures 3A, 3B, 4A, 4B, 5A, 5B:
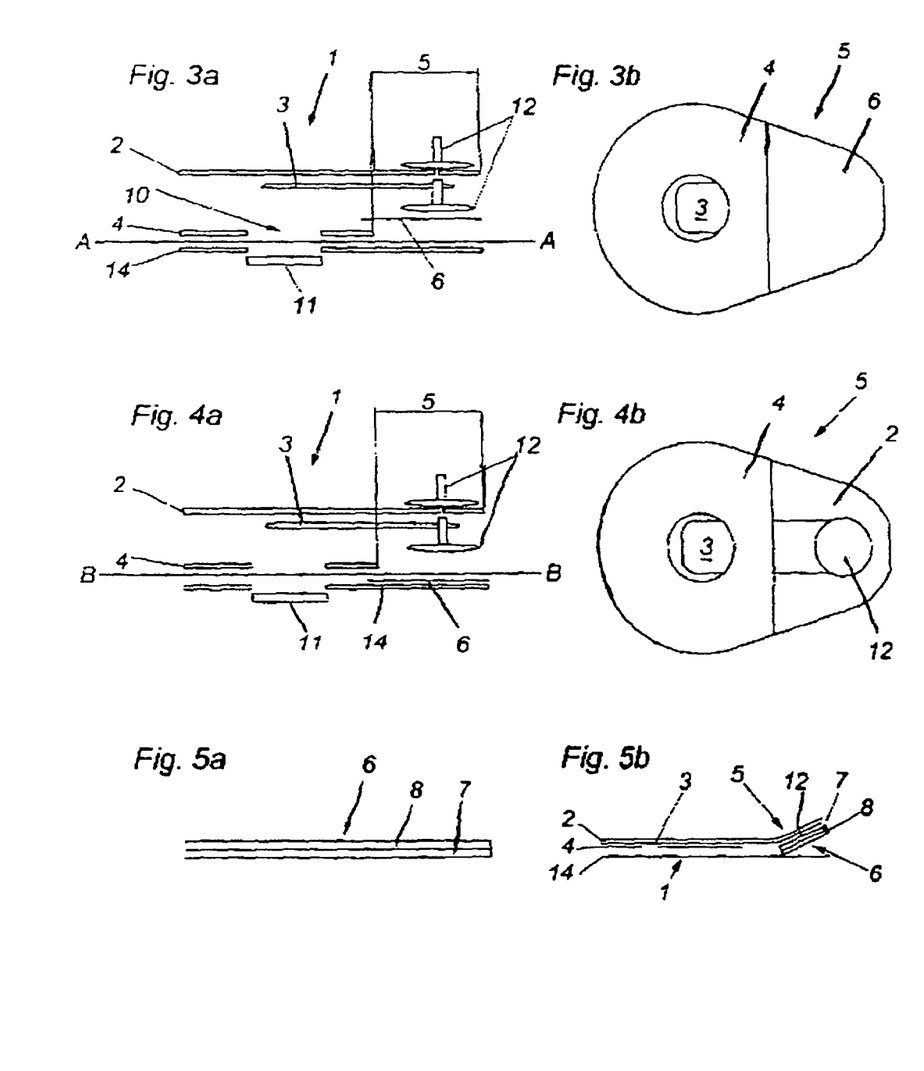
FIG. 3a to 3c show a first embodiment of the invention.
FIG. 4a to 4c show a further embodiment of the invention.
FIG. 5a shows a covering according to the invention.
FIGS. 5b and 5c show different arrangement possibilities of the covering shown in FIG. 5a on a medical electrode.
Figure 3C:
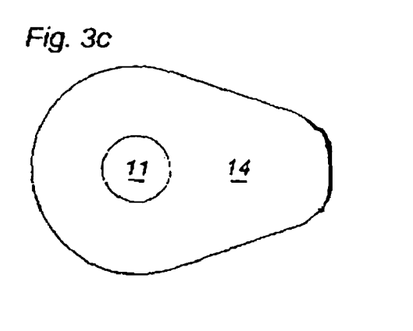

A first embodiment example of a medical electrode 1 according to the invention is shown in FIG. 3a to 3c. In this case, underneath the adhesive layer 4 on the side of the electrode 1 facing the skin of the patient there is arranged a plaster element 14 which has a through opening which approximately coincides with the opening 10 of the adhesive layer 4 and in which is arranged an electrically conductive gel 11 which establishes the contact between the skin of the patient and the signal conductor 3. A covering 6, one side of which is electrically conductive in construction, is arranged on the side of the tapping pad 5 facing the skin. This covering 6, as shown in FIG. 3b, which shows an under-view of the upper part of the medical electrode 1 along the section A-A, completely covers the tapping pad 5. The bottom side of the covering 6 which can be seen in FIG. 3b (i.e., the side closest to the skin) is electrically conductive in construction. The electrical conductivity is achieved, for example, by application of an electrically conductive foam or by printing on an electrically conductive layer.

Although an optimum electrical conductivity is achieved by the construction of the covering 6 as shown in FIG. 3b, a certain shielding effect can also be achieved if the covering 6 is constructed to mask only the part of the signal conductor 3 arranged on the tapping pad 5. FIG. 3c shows a plan view of the plaster element 14 along the intersecting line A-A, the electrically conductive gel 11 being arranged in the through-opening.

Figure 4C:
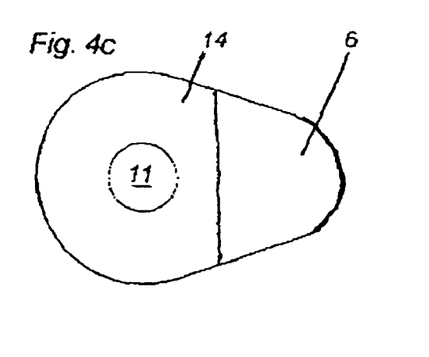

In the embodiment according to FIG. 4a to 4c, the covering 6, one side of which is electrically conductive in construction or which is conductive throughout, is arranged not on the tapping pad 5 but on the part of the plaster element 14 masking the tapping pad. In such an arrangement of the covering element 6, it is to be ensured that the electrically conductive side of the covering element 6 faces the tapping pad 5. In order to avoid contact of the covering element 6 with the signal conductor 3 or the lower part of the tapping element 12, the side of the tapping pad 5 facing the plaster element 14 can additionally be provided with an electrically insulating covering element (not shown). Analogously to FIG. 3b, FIG. 4b shows the under-view of the medical electrode 1 along the intersecting line B-B, from which it can be seen that the signal conductor 3 is arranged on the under-side of the upper top layer 2 in the region of the tapping pad 5. FIG. 4c shows the top view of the plaster element 14 along the intersecting line B-B with a covering element 6 arranged on the part of the plaster element 14 masking the tapping pad.

Figure 5C:
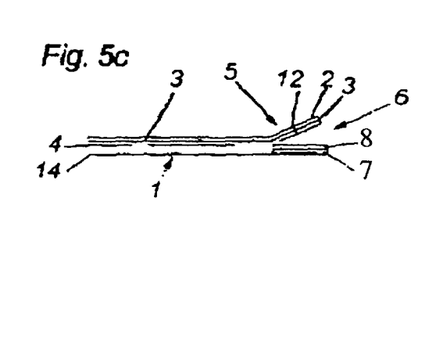

A preferred embodiment of the covering element 6 according to the invention is shown in FIG. 5a. In this case, the covering element 6 is constructed as a two-layered film and has an electrically insulating carrier layer 7 and an electrically conductive layer 8. This electrically conductive layer 8, for example, can be formed by an electrically conductive element having a grid-like construction or printed on. Construction of the electrically conductive layer 8 by means of an electrically conductive foam, a metallic strip, a textile sheet-like structure with integrated metallic threads or the like is likewise expedient Two different arrangement possibilities of a covering element 6 according to FIG. 5a on a medical electrode 1 are shown in FIGS. 5b and 5c. In the variant shown in 5b, the covering element 6 is arranged on the tapping pad 5, and indeed on the bottom side facing the skin of the patient. In this case, the covering element 6 is connected with its electrically insulating carrier layer 7 to the tapping pad 5, so that the electrically conductive layer 8 is separated galvanically from the signal conductor 3 (i.e., faces toward the skin). In the variant shown in FIG. 5c, the covering element 6 is connected to the plaster element 14, and indeed such that the electrically conductive layer 8 faces the tapping pad 5. To prevent the electrical layer 8 of the covering element 6 from coming into contact with the signal conductor 3, the tapping pad 5 can be provided, on the side facing the covering 6, with an electrically insulating covering which, for example, can be constructed in one piece with the upper top layer.

In the embodiments of the invention shown in FIG. 6a to 6c and 7a to 7c, at least the electrically conductive layer 13 on the side of the top layer 2 facing away from the skin of the patient is electrically conductive in construction.

Figure 6A:
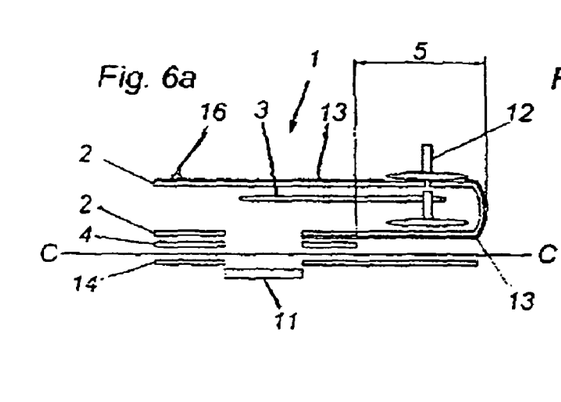
FIG. 6a to 6c show further embodiments of an electrode according to the invention with a tapping pad.
Figures 6B, 7B:
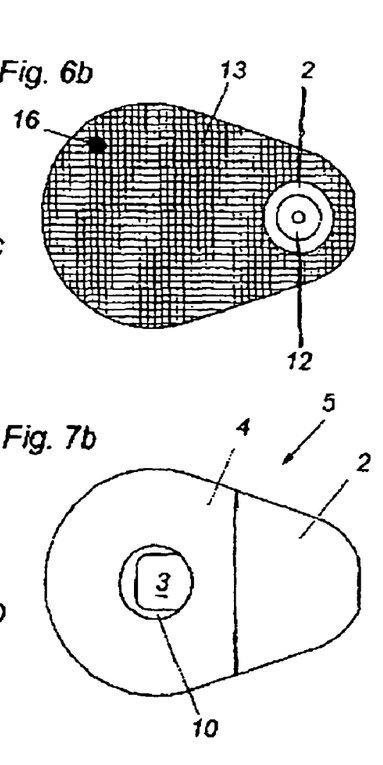
FIG. 7a to 7c show further embodiments of an electrode according to the invention with a tapping pad.
Figure 6C:
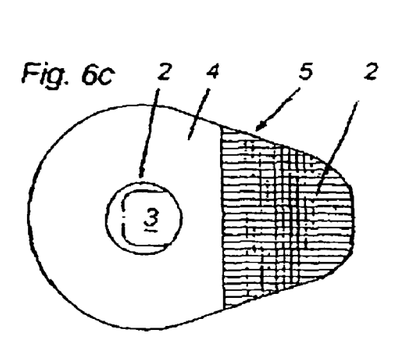
Figure 7A:
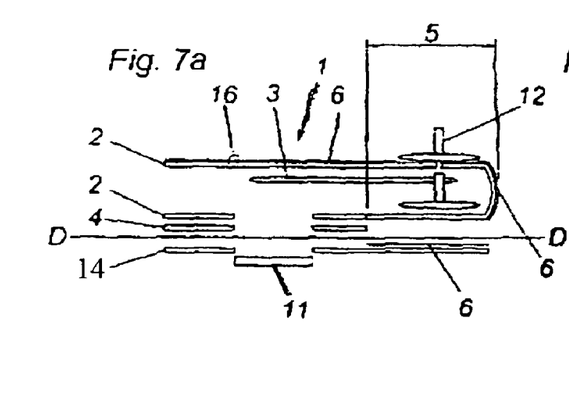
Figure 7C:
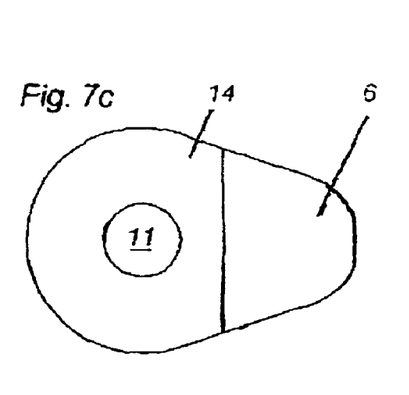

In the embodiment according to FIG. 6a to 6c, the tapping pad 5 additionally has on its side facing the skin a covering which is produced in one piece with the upper top layer 2 and is formed by this. As a result, on the one hand the electrode is covered completely or three-dimensionally and, on the other hand, the side of the tapping pad 5 facing the skin is covered specifically by an electrically conductive layer 13, so that external interference signals can be kept away from the signal conductor 3. FIG. 6b shows a plan view of the medical electrode 1 shown in FIG. 6a, from which it is seen that the electrically conductive layer 13 has a grid-like construction. The grid-like electrically conductive layer 13 extends to just before the upper part of the tapping element 12, but is not in contact with the tapping element 12, so that the top layer 2 is visible between the tapping element 12 and the electrically conductive layer 13. It can be seen from FIG. 6c, which shows an under-view of the medical electrode 1 along the intersecting line C-C, that the top layer 2 is covered by the grid-like electrically conductive layer 13 in the region of the tapping pad 5, while the remainder of the top layer 2 is covered by the adhesive layer 4 up to the opening for the electrically conductive gel 11. The connection element 16 is the earth and serves to earth the electrically conductive layer 13. It would of course also be conceivable for the side of the tapping pad 5 facing the skin, instead of the top layer 2 provided with an electrically conductive side 13, to be provided with a covering element 6 which is to be applied separately.

Where in the embodiment shown in FIG. 6a to 6c the top layer is constructed as a two-layered film having an electrically insulating top layer 2 and an electrically conductive layer 13, in contrast to this in the embodiment example shown in FIG. 7a to 7c, the upper top layer has, on its side facing away from the skin of the patient, a covering element 6 having at least one electrically conductive side. The covering element 6 is advantageously constructed in two layers, the arrangement of the covering element 6 being such that the electrically conductive side faces away from the top layer 2. The top layer 2 is turned down in the region of the tapping pad 5 and therefore covers the signal conductor 3 against external influences at least in the region of the tapping pad 5. By arrangement of the covering element 6 also along the side face of the tapping pad 5, static charging of the top layer 2, which in the normal case is produced from plastic, arranged on the under-side of the tapping pad 5 can be almost completely avoided. In addition, in the embodiment shown, a covering element 6 is arranged on the part of the plaster element 14 masking the tapping pad 5, such that the electrically conductive side of the covering element 6 faces the tapping pad 5.

It can be seen from FIG. 7b, which shows an under-view of the electrode 1 along the section D-D, that the tapping pad 5 is covered by the top layer 2 on its side facing the skin of the patient, while the remaining part of the electrode 1 is provided with an adhesive layer 4. The opening 10 in the adhesive layer 4 in turn serves to accommodate an electrically conductive gel 11, by means of which the signal conductor 3 is connected to the skin of the patient FIG. 7c shows a plan view of the plaster element 14 along the intersecting line D-D, from which it is seen that the part of the plaster element 14 masking the tapping pad 5 is provided with a covering element 6, the electrically conductive side of the covering element 6 facing the tapping pad 5. The conductive gel 11 is arranged in a through-opening of the plaster element 14 which substantially corresponds to the opening 10 in the adhesive layer 4.

Figure 8A:
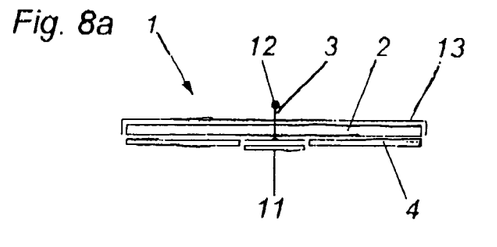
FIGS. 8a and 8b show a diagram of two embodiments of an electrode according to the invention without a tapping pad.
Figure 8B:
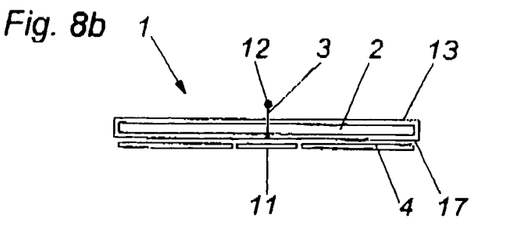

FIGS. 8a and 8b each show a medical electrode 1 without a tapping pad. In other words, the tapping element 12 lies directly over the region of the signal conductor 3 through which this electrode is in contact with the signal-emitting subject, preferably via a conductive gel 11. The top layer 2, which substantially forms the carrier of the electrode 1, has an electrically conductive layer 13 on its side facing away from the skin of the patient. An adhesive layer 4 for sticking the electrode 1 on to the skin is arranged at least in regions on the side of the top layer 2 facing the skin. The electrically conductive layer 13 has a conducting action so that the build up of a static charge, which could influence the signal conducted, is prevented. In the embodiment example according to FIG. 8b, an electrically conductive layer 17 is likewise arranged on the side of the top layer 2 facing the skin of the patient, between the top layer 2 and the adhesive layer 4, so that the top layer 2 is enclosed on all sides (three-dimensionally, by an electrically conductive layer 13) 17 for conducting interference signals.

Figure 9A:
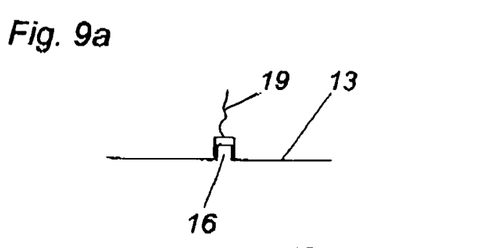
FIGS. 9a and 9b show a diagram of different fixing possibilities of the conductor for the interference signal to the electrical layer.
Figure 9B:
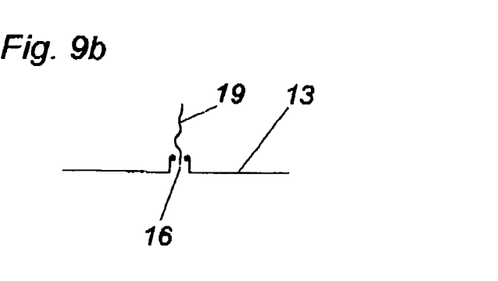

Two different possibilities of a plug connection between a connection element 16 of the electrically conductive layer 13 and a conductor 19 for conducting the interference signals are shown in FIGS. 9a and 9b. According to FIG. 9a, the connection element 16 is constructed, for example, in the nature of a pushbutton. The conductor 19 is constructed in the form of a cap at its end and is pushed on to the connection element 16. In contrast to this, the connection element 16 according to FIG. 9b has an opening into which the conductor 19 is pushed.

In this case the connection element 16 can be sprung in construction, so that the conductor 19 can be held locked in the manner of a clamp.

Figure 10:
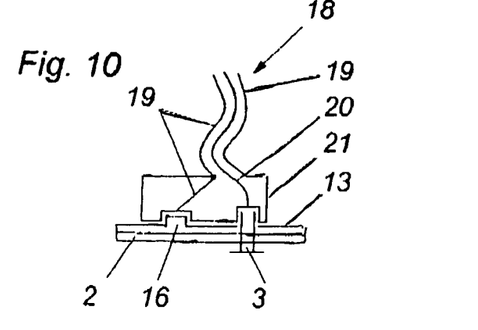
FIGS. 10 and 11 show different connection possibilities of the lead for conducting the signals to the electrode.

In the embodiment shown in FIG. 10, the lead 18 is constructed as a coaxial cable and has a connection element 21 with which the connection element 16 of the electrically conductive layer 13 and the signal conductor 3 can be contacted simultaneously. In this case the outer of the two conductors 19 forms the shield for the conductor 20 connected to the signal conductor 3 and at the same time the housing of the connection element 21 or is connected to this electrically. In this manner, the conductor 19 is the ground for the electrically conductive layer 13. The conductor 20 by means of which the measurement signal is conducted from the signal conductor 3 is separated galvanically from the conductor 19 or from the housing 21 and therefore from the electrically conductive layer 13.

Figure 11:
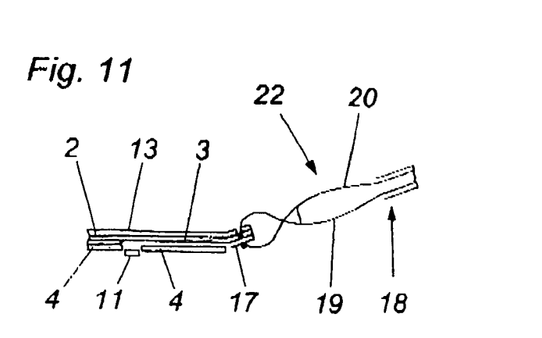

In the embodiment according to FIG. 11, both the interference signal and the measurement signal are led away via a clamp device 22, for example a crocodile clip 22. In this case, one clamp part 19 grips the electrically conductive layer 17 which serves to shield the signal conductor 3, while the second clamp part 20, which is separated galvanically from the first clamp part 19, grips the signal conductor 3 directly and transmits the measurement signal in this manner.

Although the invention has been described in detail with the aid of the embodiments shown, it goes without saying that the invention is not limited to the embodiments shown. Rather, all possible combinations of the embodiments described in the claims and in the figures which are capable of converting a fundamental idea of the invention, namely the creation of a medical electrode in which the actual signal conductor is kept free from interference signals by means of an additional electrically conductive layer in accordance with the principle of a Faraday shield or cup, are claimed.

The invention claimed is:

1. A medical electrode for conducting signals, said electrode comprising:
   a upper top layer;
   an adhesive layer to be brought into contact with a signal-emitting subject;
   a signal conductor to be connected to the signal-emitting subject, said signal conductor being arranged between said upper top layer and said adhesive layer;
   a tapping pad between said upper top layer and the signal-emitting subject; and
   a covering element to be arranged between said tapping pad and the signal-emitting subject so as to cover said tapping pad, said covering element including an electrically insulating layer and having an electrically conductive side, wherein said signal conductor and said electrically conductive side of said covering element are separated galvanically and are arranged vertically spaced from one another.

2. The electrode of claim 1, wherein said electrically conductive side of said covering element comprises an electrically conductive element having a grid construction.

3. The electrode of claim 1, wherein said electrically conductive side of said covering element comprises an electrically conductive foam.

4. The electrode of claim 1, wherein said covering element comprises a film, said electrically insulating layer comprising an electrically insulating carrier layer of said film, said film further including an electrically conductive layer.

5. The electrode of claim 4, wherein said covering element comprises a two-layered film.

6. The electrode of claim 1, wherein said signal conductor and said electrically conductive side of said covering element have an overlapping region.

7. The electrode of claim 1, wherein said signal conductor is to be connected to the signal-emitting subject via an electrically conductive gel.

8. The electrode of claim 7, wherein said electrically conductive gel is located in an opening of said adhesive layer.

9. The electrode of claim 1, wherein said tapping pad has a tapping element electrically contacting said signal conductor, said tapping element being accessible from a side of said electrode facing away from the signal-emitting subject.

10. The electrode of claim 9, wherein said tapping element is formed as a stud.

11. The electrode of claim 1, wherein said covering element is connected to said tapping pad.

12. The electrode of claim 1, wherein said covering element includes a carrier layer, at least said carrier layer of said covering element being constructed as one piece with said upper top layer.

13. The electrode of claim 12, wherein at least a portion of said electrically conductive side of said covering element extends to an upper side of said upper top layer.

14. The electrode of claim 1, further comprising at least one electrically conductive layer separated galvanically from said signal conductor and arranged to be brought into contact with a conductor for conducting the interference signals or for grounding.

15. The electrode of claim 14, further comprising a connection element is arranged on said at least one electrically conductive layer or connected to said at least one electrically conductive layer so as to detachably fix the conductor to said at least one electrically conductive layer.

16. The electrode of claim 14, wherein a signals of said signal conductor and interference signals of said at least one electrically conductive layer are transmitted via a lead having two galvanically separated conductors.

17. The electrode of claim 16, wherein said two conductors of said lead are coaxial, an inner conductor of said two coaxial conductors contacting said signal conductor.

18. The electrode of claim 16, wherein said lead has a connection element for bringing said at least one electrically conductive layer and said signal conductor into contact simultaneously with corresponding conductors of said lead.

19. The electrode of claim 1, wherein said signal conductor is metallic, and is shaped and arranged to be connected to the signal-emitting subject.

20. The electrode of claim 1, wherein said signal conductor comprises a signal-conducting layer.

21. The electrode of claim 1, wherein said covering element is planar.

22. The electrode of claim 1, further comprising at least one electrically conductive layer, each of said at least one electrically conductive layer comprising a Faraday shield or cup.

23. A medical electrode for conducting signals, said electrode comprising:
   a upper top layer;
   an adhesive layer to be brought into contact with a signal-emitting subject;
   a signal conductor to be connected to the signal-emitting subject, said signal conductor being arranged between said upper top layer and said adhesive layer;
   a tapping pad between said upper top layer and the signal-emitting subject; and
   a covering element to be arranged between said tapping pad and the signal-emitting subject so as to cover said tapping pad, said covering element including an electrically insulating layer and having an electrically conductive side separated galvanically from said signal conductor, and an electrically insulating plaster element arranged on a side of said adhesive layer to be facing the signal-emitting subject.

24. The electrode of claim 23, wherein said electrically insulating layer comprises an electrically insulating carrier layer, at least said electrically insulating carrier layer of said covering element is formed of said plaster element.

25. The electrode of claim 23, wherein said plaster element has at least a portion masking said tapping pad, said at least a portion of said plaster element having an electrically conductive side facing said tapping pad.

26. A medical electrode for conducting signals, said electrode comprising:

a upper top layer;

an adhesive layer to be brought into contact with a signal-emitting subject;

a signal conductor to be connected to the signal-emitting subject, said signal conductor being arranged between said upper top layer and said adhesive layer;

a tapping pad between said upper top layer and the signal-emitting subject; and a covering element to be arranged between said tapping pad and the signal-emitting subject so as to cover said tapping pad, said covering element including an electrically insulating layer and having an electrically conductive side separated galvanically from said signal conductor, wherein said upper top layer has an upper side to be facing away from the signal-emitting subject, said upper side of said upper top layer having at least an electrically conductive region.

27. The electrode of claim 26, wherein said upper top layer further has an under side with at least an electrically conductive region.

28. The electrode of claim 26, wherein said electrically conductive region of said upper side of said upper top layer comprises an electrically conductive element having a grid construction.

29. The electrode of claim 26, wherein said electrically conductive region of said upper side of said upper top layer comprises an electrically conductive foam.

30. The electrode of claim 26, wherein said electrically conductive region of said upper side of said upper top layer comprises a printed-on electrically conductive layer.

31. The electrode of claim 26, wherein said upper top layer comprises a film including an electrically insulating carrier layer and an electrically conductive layer.

32. The electrode of claim 31, wherein said upper top layer comprises a two-layered film.

33. The electrode of claim 26, wherein said electrically conductive region of said upper side of said upper top layer comprises a film including an electrically insulating carrier layer and an electrically conductive layer.

34. The electrode of claim 33, wherein said electrically conductive region of said upper side of said upper top layer comprises a two-layered film.

35. The electrode of claim 26, wherein said electrically conductive region of said upper side of said upper top layer is separated galvanically from said signal conductor.

36. The electrode of claim 35, wherein said electrically conductive region of said upper side of said upper top layer comprises one of a plurality of separate electrically conductive regions of said upper side of said upper top layer, said separate electrically conductive regions of said upper side of said upper top layer are connected electrically to one another.

37. The electrode of claim 26, wherein said electrically conductive region of said upper side of said upper top layer, said signal conductor, and said electrically conductive side of said covering element are arranged vertically spaced from one another.

38. The electrode of claim 37, wherein said electrically conductive region of said upper side of said upper top layer, said signal conductor, and said electrically conductive side of said covering element at least partially overlap.

* * * * *